(12) United States Patent
McCook et al.

(10) Patent No.: US 8,182,794 B2
(45) Date of Patent: May 22, 2012

(54) SUNLESS TANNING PRODUCTS AND PROCESSES

(75) Inventors: John Patrick McCook, Frisco, TX (US); Philip J. Gordon, Plano, TX (US); D. Craig Woodward, Plano, TX (US)

(73) Assignee: Concept Laboratories

( * ) Notice: Subject to any disclaimer, the term of this patent is extended or adjusted under 35 U.S.C. 154(b) by 548 days.

(21) Appl. No.: 11/394,940

(22) Filed: Apr. 1, 2006

(65) Prior Publication Data

US 2006/0177398 A1 Aug. 10, 2006

Related U.S. Application Data

(63) Continuation-in-part of application No. 10/382,686, filed on Mar. 5, 2003, now abandoned.

(51) Int. Cl.
*A61K 8/00* (2006.01)
*A61K 8/18* (2006.01)
*A61K 31/12* (2006.01)
*A61K 31/045* (2006.01)
*A61K 31/74* (2006.01)
*A61K 31/10* (2006.01)
*A61Q 17/04* (2006.01)
*A01N 35/00* (2006.01)
*A01N 31/00* (2006.01)
*A01N 41/10* (2006.01)

(52) U.S. Cl. ....... 424/59; 424/78.03; 514/675; 514/724; 514/709; 514/738

(58) Field of Classification Search ............... 424/59, 424/78.03; 514/675, 724, 738, 709
See application file for complete search history.

(56) References Cited

U.S. PATENT DOCUMENTS

| 4,296,130 | A | * | 10/1981 | Herschler | 514/711 |
| 5,496,489 | A | * | 3/1996 | Dussault et al. | 252/134 |
| 6,113,888 | A | * | 9/2000 | Castro et al. | 424/59 |
| 6,231,837 | B1 | * | 5/2001 | Stroud et al. | 424/59 |

FOREIGN PATENT DOCUMENTS

CA 2286408 * 3/2001

* cited by examiner

*Primary Examiner* — Johann Richter
*Assistant Examiner* — Mei-Ping Chui
(74) *Attorney, Agent, or Firm* — Louis C. Paul

(57) ABSTRACT

Sunless tanning compositions are substantially improved by adding methylsulfonyl methane [MSM] and certain glycols to Dihydroxyacetone (DHA).

8 Claims, No Drawings

SUNLESS TANNING PRODUCTS AND PROCESSES

This application is a continuation-in-part of application Ser. No. 10/382,686 filed Mar. 5, 2003 now abandoned bearing the same title.

BACKGROUND OF THE INVENTION

1. Field of the Invention

The invention describes new compositions of sunless tanning formulations that contain methylsulfonyl methane (MSM), also known as methylsulfonylmethane and as methyl sulfone, in combination with certain glycols to produce a darker, longer-lasting, natural-looking and low odor sunless tan.

2. Related Art

Sunless tanning, also called self-tanning, is the ability to impart a tan to fair or light skin without the use of sunlight. In order to achieve a tanned look or otherwise darken their skin, individuals can expose their skin to sunlight or a source of simulated sunlight, e.g., a solar simulator or ultraviolet lamps. For many individuals, such exposure will stimulate formation of new melanin pigment and retention or increased amount of melanin in the epidermis and produce a darkened skin color. However, some individuals find that such exposure does not produce the desired melanin formation and as a result the desired tan is not obtained. It is also well known that, as light skin humans age, the ability to produce melanin through ultraviolet light stimulation diminishes significantly. Additionally, exposure to the sun or a source of ultraviolet radiation can have deleterious effects for many individuals and can, in fact, cause sunburn, skin blistering, premature skin aging or skin cancer. Self-tanning or sunless tanning compositions offer a safe alternative and enable these individuals to obtain the desired tanned look.

Commercial sunless tanning formulations, using dihydroxyacetone [DHA], or DHA in combination with other reducing sugars such as 1,3,4-trihydroxy-2-butanone (erythrulose), applied locally to the skin, were developed for this purpose.

In U.S. Pat. No. 6,706,257, issued Mar. 16, 2004, McCook et al showed that sunless tanning compositions are substantially improved by adding methylsulfonyl methane [MSM] sequentially or simultaneously to compositions containing dihydroxyacetone. The McCook patent reference further shows that the enhancement of the DHA response is optimized by the inclusion of about 5% by weight of MSM to DHA sunless tanning compositions.

Prior to the McCook patent teaching, MSM had been used as a nutritional supplement when taken orally, as a topical and systemic anti-arthritis treatment and as a topical moisturizer or skin softener. The topical moisturizing or skin softening properties of MSM are described in several publications, e.g., by U.S. Pat. No. 4,296,130 to Herschler.

SUMMARY OF THE INVENTION

In U.S. Pat. No. 6,706,257, we demonstrated that the addition of MSM to sunless tanning compositions containing DHA would enhance the tanning response of DHA.

Further experimentation has shown that the inclusion of certain humectants or glycols, together with MSM will produce an enhanced tanning response, greater than that obtained through the use of either MSM or the glycol ingredient alone. Testing has focused on determining the influence of glycol-type humectant moisturizers commonly used in sunless tanning formulations. Although many of these glycol materials have been used in commercial sunless tanning formulations or have been disclosed for use in sunless tanning compositions by the patent or supplier literature, none of these glycol materials have been evaluated in conjunction with MSM or in combination with MSM and DHA.

Experimentation focused on glycols that may enhance or have a synergistic effect upon the tanning response of DHA and MSM.

Table 1 shows a first series of humectant and penetrant materials used in combination with 5% DHA and 5% MSM. In this table and all subsequent tables and examples, ingredient percentages listed are percent by weight, unless otherwise noted.

Examples included typically used 5% MSM since prior experimentation cited in U.S. Pat. No. 6,706,257 had found that 5% MSM gave the optimum tanning response. The amount of DHA included in the formula examples is 5% since typical retail commercial sunless tanning formulations (creams, lotions, gels, mousse, sprays, etc.) contain 4-6% by weight DHA. The amount of glycol chosen for the experiments was also 5% based on common usage levels as moisturizing additives and recommendations by manufacturers of these glycol materials.

TABLE 1

| Ingredients | Formula % W/W | | | | | | | |
|---|---|---|---|---|---|---|---|---|
| | A | B | C | D | E | F | G | H |
| MSM | 5 | 5 | 5 | 5 | 5 | — | — | — |
| DHA | 5 | 5 | 5 | 5 | 5 | 5 | 5 | — |
| Propylene Glycol | — | 5 | — | — | — | — | — | — |
| Butylene Glycol | — | — | 5 | — | — | — | — | — |
| Glycerin | — | — | — | 5 | — | — | — | — |
| Pentylene Glycol | — | — | — | — | 5 | — | — | — |
| Erythrulose | — | — | — | — | — | 5 | — | 5 |
| Citric Acid Solution | * | * | * | * | * | * | * | * |
| Water, Deionized | 90 | 85 | 85 | 85 | 85 | 90 | 95 | 95 |
| Total | 100 | 100 | 100 | 100 | 100 | 100 | 100 | 100 |

*Solutions are adjusted to a pH of 3.0-3.5

An equal amount of each formula solution (approximately 150 mg.) from Table 1 was applied to 2"×2" adjacent sections of forearm, allowed to dry and covered with clothing for the duration of the testing. The application areas were visibly the same color prior to treatment with the solutions and this was confirmed via calorimeter readings. Readings were typically made 24-48 hours post application of the test solutions. Three calorimeter readings were made of each treatment area with a Minolta CR-10 adapted for human skin readings and the readings were averaged. All eight formulas shown in Table 1 were evaluated on several individuals with Fitzpatrick skin types I-III. Although the absolute values for the tanning responses differed between individuals, the relative differences between formulations in terms of tanning response were the same. Typical results of the testing of one subject were recorded in average L* a* b* color values and are shown in Table 2 along with baseline skin color.

TABLE 2

| Formula | L | a | b |
|---|---|---|---|
| A | 58.6 | 12.5 | 15.9 |
| B | 56.3 | 12.2 | 16.1 |
| C | 57.4 | 13.3 | 16.8 |
| D | 58.1 | 11.1 | 14.1 |
| E | 57.7 | 13.8 | 15.5 |
| F | 59.6 | 12.4 | 15.2 |
| G | 58.7 | 11.8 | 14.1 |
| H | 63.7 | 9.6 | 13.0 |
| Baseline | 63.9 | 9.9 | 9.3 |

The test results shown in Table 2 indicate no significant tanning response from erythrulose (Formula "H") with the darker tanning responses coming from the addition of propylene glycol, butylene glycol, or pentylene glycol to combinations of MSM and DHA.

In this series shown in Table 2—formulas C and E with butylene glycol or pentylene glycol, respectively, added to DHA and MSM give the most natural looking tan based on calculations of the hue intensity (square root of a* squared plus b* squared) and the hue balance (b*/a*).

The tanning response of the formulas in Table 2 were further analyzed to determine the increase in the tanning response. Using color theory recommendations published by Konica Minolta Corporation (Tokyo, Japan) and others, the Minolta CR-10 Colorimeter L a* b* values obtained were translated into changes in skin darkness, hue intensity and overall tan. The results of these calculations are shown in Table 3 below:

TABLE 3

| Formula | Darkness increase ($\Delta L$) | Hue increase $\Delta\sqrt{a^2 + b^2}$ | Tan Increase $(\Delta L) + \Delta\sqrt{a^2 + b^2}$ |
|---|---|---|---|
| G (DHA control) | 5.2 | 4.8 | 10.0 |
| A (DHA + MSM) | 5.3 | 6.6 | 11.9 |
| C (Formula A + Butylene Glycol) | 6.5 | 7.8 | 14.3 |
| E (Formula A + Pentylene Glycol) | 6.2 | 7.2 | 13.4 |
| D (Formula A + Glycerin) | 5.8 | 4.4 | 10.2 |

The formulations shown in Table 2 were evaluated several times over the course of several weeks with 3-4 subjects each time with readings taken at 24 or 48 hours post application. Results obtained were consistent with the findings depicted in Table 3. It is quite interesting that glycerin (formula D) exhibits a very poor tanning response when compared to the other glycols tested. Glycerin is a well known skin softener, humectant, and moisturizer, used world-wide over the last 100 years in skin care topical treatment products and currently used in products throughout the Cosmetic and Pharmaceutical Industries for its skin softening and moisturizing properties. Glycerin is frequently used as a moisturizer in commercial sunless tanning products. However, glycerin does not enhance the tanning response when compared to the combination of MSM and certain other glycols as shown in Table 3. In fact, glycerin has an inhibitory effect on the tanning response of DHA and MSM. Although the skin moisturizing and humectant properties of glycerin are well known, additives that improve or enhance skin moisturization, skin softening, or skin humectancy, or are otherwise used to prevent skin drying, do not necessarily enhance the sunless tanning response, i.e., produce darker, longer-lasting and more natural looking tans. In the case of glycerin, this common moisturizing additive does not enhance the DHA tan response and is inhibitory to MSM, a compound that has been shown to enhance the tanning response of DHA. Note especially the results of the calculation of hue intensity for the formulations in Table 3.

Hue intensity is regarded as the most sensitive measurement for evaluating skin tanning. In this regard, glycerin shows no significant change over the control and inhibits the tanning increase seen with the addition of MSM. In these experiments, both butylene glycol and pentylene glycol significantly increase the tanning response of DHA & MSM.

Butylene glycol is a water soluble or water miscible humectant, moisturizer, and solubilizer that has been used in topical cosmetic and pharmaceutical products for decades. It is used frequently in topical cosmetic or skin care formulations, including sunless tanning formulations, to increase the moisturizing properties of these formulas.

Pentylene glycol or 1,2-pentanediol, supplied as Hydrolite-5 by Symrise GmbH & Co., Holzminden, Germany, has, within the last decade, been offered for sale for use as a moisturizing humectant, primarily for skin care product use. U.S. Pat. No. 6,113,888 issued to Castro et al on Sep. 5, 2000 describes sunless tanning mousse compositions containing DHA and various humectants which can include 1,2-pentanediol. U.S. Pat. No. 6,214,322 issued to Castro, et al on Apr. 10, 2001 describe sunless tanning compositions containing carmine that may also contain 1,2-pentanediol as a humectant. In the Castro patent examples as well as other published information on sunless tanning formulations, no special significance, beyond the moisturization function, is attributed to the inclusion of humectant moisturizers such as sorbitol, glycerin, glycereth 5 lactate, glycereth 7 triacetate, glycereth 7 diisononoate, hexanetriol, methyl-propanediol, 1,2-pentanediol, hexylene glycol, propylene glycol, alkoxylated glucose, D-panthenol and derivatives thereof, hyaluronic acid as well as other humectants listed in the International Cosmetic Ingredient Dictionary and Handbook published by The Cosmetic, Toiletry, and Fragrance Association (CTFA, Washington, D.C.). However, as we have shown in Tables 1-3, and as we shall demonstrate in further experiments detailed below, the choice of humectant can greatly influence the prime performance attributes of a sunless tanning formula; namely, the development of a dark, long-lasting and natural-looking tan.

Based on the results described in Table 3, a second series of experiments explored the tanning properties of MSM & DHA when combined with the glycols from Table 1, as well as with ethoxydiglycol, when used alone or in combination. Concentrations of DHA and MSM were maintained at 5% by weight and the various glycols were evaluated singly or in combination at concentrations of 4% or 8% to determine the affect on the DHA/MSM mix. The evaluation of formulations in Table 4 below were conducted to determine the relative ability of the selected glycols to enhance the tanning response of mix of DHA and MSM. Formulations I and J are repeat runs of the same formulation on the same subject. The results in Table 4 are illustrative and representative of the results obtained after testing the same series of formulations on several subjects.

TABLE 4

| Ingredients | Formula % W/W | | | | | | | | | |
|---|---|---|---|---|---|---|---|---|---|---|
| | A | B | C | D | E | F | G | H | I | J |
| MSM | 5 | 5 | 5 | 5 | 5 | 5 | 5 | 5 | 5 | 5 |
| DHA | 5 | 5 | 5 | 5 | 5 | 5 | 5 | 5 | 5 | 5 |
| Propylene Glycol | 4 | 4 | — | — | 4 | — | — | — | — | — |
| 1,3-Butylene Glycol | 4 | — | 8 | 4 | — | — | — | — | 4 | 4 |
| Ethoxydiglycol | — | — | — | 4 | 4 | 8 | — | 4 | — | — |
| Pentylene Glycol | — | 4 | — | — | — | — | 8 | 4 | 4 | 4 |
| Citric Acid Solution | * | * | * | * | * | * | * | * | * | * |
| Water, Deionized | 82 | 82 | 82 | 82 | 82 | 82 | 82 | 82 | 82 | 82 |
| Total | 100 | 100 | 100 | 100 | 100 | 100 | 100 | 100 | 100 | 100 |

Solutions are adjusted to a pH of 3.0-3.5

An equal amount of each formula (approximately 150 mg.) from Table 3 was applied to 2"×2" adjacent sections of forearm, allowed to dry and covered with clothing for the duration of the testing. The application areas were visibly the same color prior to treatment with the solutions and this was confirmed via colorimeter readings. Several colorimeter readings were made of each treatment area with a Minolta CR-10 adapted for human skin readings. Results of the testing were recorded in average L* a* b* color values and are shown in Table 5.

TABLE 5

| Formula | L | a | b |
|---|---|---|---|
| A | 60.2 | 11.3 | 16.6 |
| B | 58.3 | 12.7 | 18.2 |
| C | 59.7 | 12.2 | 18.1 |
| D | 58.2 | 11.8 | 17.4 |
| E | 58.7 | 11.3 | 18.5 |
| F | 59.6 | 11.9 | 16.7 |
| G | 55.5 | 13.3 | 18.0 |
| H | 56.6 | 13.3 | 17.1 |
| I | 56.2 | 14.4 | 17.1 |
| J | 55.9 | 13.5 | 18.2 |

Formulas G through J in Table 4 that contain pentylene glycol alone or mixtures of pentylene glycol with 1,3-butylene glycol or pentylene glycol with ethoxydiglycol developed a darker, more intense, longer lasting and more natural looking tan with DHA and MSM than the other humectants alone based on analysis of hue balance, hue intensity and overall tanning response.

In Table 6 below, the addition of pentylene glycol to DHA and MSM was compared to the addition of MP Diol (2-methyl-1,3-propanediol; Barnet) ethoxydiglycol, and hexylene glycol plus DHA and MSM versus a DHA/erythrulose/MSM control.

TABLE 6

| Ingredient | Formula (% w/w) | | | | |
|---|---|---|---|---|---|
| | A | B | C | D | E |
| DHA | 5 | 5 | 5 | 5 | 5 |
| MSM | 5 | 5 | 5 | 5 | 5 |
| Pentylene Glycol | 5 | — | — | — | — |
| Hexylene Glycol | — | 5 | — | — | — |
| MP Diol | — | — | 5 | — | — |
| Ethoxydiglycol | — | — | — | 5 | — |
| Erythrulose | — | — | — | — | 5 |
| Citric acid solution | * | * | * | * | * |
| Water, Deionized | 85 | 85 | 85 | 85 | 85 |

* Solutions are adjusted to a pH of 3.0-3.5

An equal amount of each formula (approximately 150 mg.) from Table 5 was applied to 2"×2" adjacent sections of forearm, allowed to dry and covered with clothing for the duration of the testing. The application areas were visibly the same color prior to treatment with the solutions and this was confirmed via calorimeter readings. Instead of objective colorimeter readings, visual assessment of the sunless tan color development was made by trained experts 24-48 hours post application using a 0-10 point scale with 0 signifying no color development versus non-treated skin, 5 signifying moderate color development and 10 signifying intensely dark color development. Typical sunless tan color development scoring for this group of formulations is shown in Table 7 and is representative of several repeat studies on separate groups of test subjects.

TABLE 7

| Formula | Rating; subject 1 | Rating; subject 2 |
|---|---|---|
| A | 6.0 | 6.0 |
| B | 5.0 | 3.0 |
| C | 3.0 | 4.0 |
| D | 4.0 | 5.0 |
| E | 4.0 | 1.0 |

Again, the formulation containing pentylene glycol gives a more intense tanning response when used with MSM and DHA., as judged visually. Additionally, further evaluation of the formulas in Table 6 over the course of 7 days post application, showed the formula containing DHA/MSM/pentylene glycol produced a longer lasting tan than the other formulas in Table 6.

Additional experiments explored the tanning response of combinations of pentylene glycol (Hydrolite-5; Symrise, Inc.) with other glycols and with the skin penetrant dimethyl isosorbide (DMI), not previously tested with DHA and MSM. These formulas are shown in Table 8.

TABLE 8

| Ingredient/Formula | A | B | C | D | F | G | H | I |
|---|---|---|---|---|---|---|---|---|
| DHA | 5 | 5 | 5 | 5 | 5 | 5 | 5 | 5 |
| MSM | 5 | 5 | 5 | 5 | 5 | 5 | 5 | 5 |
| Hexylene Glycol | — | 4 | — | — | — | — | — | — |
| Pentylene Glycol | 8 | 4 | — | 4 | — | 4 | — | 4 |
| Dimethyl Isosorbide | — | — | 8 | 4 | — | — | — | — |
| Isopentyl Diol | — | — | — | — | — | — | 8 | 4 |

TABLE 8-continued

| Ingredient/Formula | A | B | C | D | F | G | H | I |
|---|---|---|---|---|---|---|---|---|
| Prisorene 2034** | — | — | — | — | 8 | 4 | — | — |
| Citric Acid Solution | * | * | * | * | * | * | * | * |
| Water, Deionized | 82 | 82 | 82 | 82 | 82 | 82 | 82 | 82 |
| Totals | 100 | 100 | 100 | 100 | 100 | 100 | 100 | 100 |

*Solutions are adjusted to a pH of 3.0-3.5
**Propylene Glycol Monoisostearate (Uniquema)

An equal amount (approximately 150 mg.) of each formula solution from Table 8 was applied to 2"×2" adjacent sections of forearm, allowed to dry and covered with clothing for the duration of the testing. The application areas were visibly the same color prior to treatment with the solutions and this was confirmed via colorimeter readings. Several colorimeter readings were made of each treatment area with a Minolta CR-10 adapted for human skin readings. Results of the testing were recorded in average L* a* b* color values and the results are shown in Table 9 and are representative of the results of several tests of the same formulations on several individual test subjects.

TABLE 9

| Formula | L | a | b |
|---|---|---|---|
| A | 57.2 | 12.5 | 19.0 |
| B | 58.1 | 12.0 | 19.3 |
| C | 58.0 | 12.1 | 18.1 |
| D | 57.4 | 12.0 | 19.0 |
| F | * | * | * |
| G | * | * | * |
| H | 55.6 | 12.4 | 19.8 |
| I | 54.9 | 12.0 | 19.1 |

* Incompatibility noted-Incomplete and uneven color development due to incomplete solubility of Prisorine 2034.

The results in Table 9 were analyzed by comparing changes in the hue intensity and overall tanning response. Formulations containing pentylene glycol, or pentylene glycol mixed with hexylene glycol, dimethyl isosorbide (Arlasolve DMI; ICI), or isopentyl diol (Isoprene Glycol; Barnet) show enhanced darkening based on comparisons made to previous studies. Visual assessment of the tanning response ranked formulas A, B, and I (pentylene glycol or mix of pentylene glycol) as giving the darkest, most intense response. Repeat testing on several individuals gave the same overall results.

Other experiments evaluated the tanning response of 0-10% pentylene glycol in combination with MSM and DHA are shown in Table 10.

TABLE 10

| | Formula (% w/w) | | | | | |
|---|---|---|---|---|---|---|
| Ingredient | B | G | H | I | J | K |
| DHA | 5 | 5 | 5 | 5 | 5 | 5 |
| MSM | 5 | — | — | 10 | 5 | 10 |
| Pentylene Glycol | — | 5 | 10 | — | 10 | 5 |
| Citric Acid Solution | * | * | * | * | * | * |
| Water, Deionized | 90 | 90 | 85 | 85 | 80 | 80 |

*Solutions are adjusted to a pH of 3.0-3.5

An equal amount (approximately 150 mg.) of each formula from Table 10 was applied to 2"×2" adjacent sections of forearm, allowed to dry and covered with clothing for the duration of the testing. The application areas were visibly the same color prior to treatment with the solutions and this was confirmed via calorimeter readings. The tanning response for each area was visually ranked 24-48 hours after the initial application from darkest to lightest and repeated several times by several panelists. Typically, the darkest site was visually judged as more than twice as dark as the lightest site. In all cases Formula J was darkest and Formula I was the lightest when judged at 24 and 48 hours post application. Typical rankings were J>H>B>K>G>I. Again, the results confirm that MSM enhances DHA and that this enhancement is concentration or ratio dependent and that DHA/MSM is further enhanced by pentylene glycol; 10% pentylene glycol better than 5% pentylene glycol when used together with 5% MSM and 5% DHA.

Further experimentation was conducted to evaluate the affect of sorbitol, erythrulose and diglycerol versus pentylene glycol and isopentyl glycol on the tanning response of DHA and DHA/MSM with formulas shown in Table 11. Formulas not shown in this series were found to be incompatible with some component of the formulation.

TABLE 11

| | Formula (% w/w) | | | | | | | |
|---|---|---|---|---|---|---|---|---|
| Ingredient | A | B | C | D | E | G | H | J |
| MSM | 5 | 5 | 5 | 5 | 5 | 5 | — | 5 |
| DHA | 5 | 5 | 5 | 5 | 5 | 5 | 5 | 5 |
| Sorbitol, 70% | — | — | — | 7 | — | — | — | — |
| Diglycerol | — | — | 5 | — | — | — | — | — |
| Erythrulose | — | — | — | — | — | 2.5 | 2.5 | 5 |
| Isopentyl Diol | 5 | — | — | — | — | — | — | — |
| Pentylene Glycol | — | 5 | — | — | — | — | — | — |
| Citric Acid solution | * | * | * | * | * | * | * | * |
| Water, Deionized | 85 | 85 | 85 | 83 | 90 | 87.5 | 92.5 | 85 |

*Solutions are adjusted to a pH of 3.0-3.5

An equal amount (approximately 150 mg.) of each formula solution from Table 11 was applied to 2"×2" adjacent sections of forearm, allowed to dry and covered with clothing for the duration of the testing. The application areas were visibly the same color prior to treatment with the solutions and this was confirmed via calorimeter readings. Several colorimeter readings were made of each treatment area with a Minolta CR-10 adapted for human skin readings. Results of the testing were recorded in average L* a* b* color values and are shown in Table 12.

TABLE 12

| Formula | L | a | b |
|---|---|---|---|
| A | 56.0 | 14.0 | 17.3 |
| B | 57.0 | 13.9 | 18.1 |
| C | 58.3 | 12.0 | 15.0 |
| D | 57.6 | 11.7 | 15.3 |
| E | 57.2 | 13.0 | 15.2 |
| G | 57.2 | 12.2 | 16.7 |
| H | 57.3 | 12.8 | 16.8 |
| J | 57.1 | 11.0 | 16.6 |
| Baseline A-D | 60.4 | 9.6 | 11.3 |
| Baseline E-J | 61.2 | 11.2 | 12.8 |

The results shown in Table 12 were confirmed by several repeat experiments conducted on several relatively light-skin individuals (Fitzpatrick Type I-III). Analysis of the tanning response of formulations from Table 11 and 12 is shown in Table 13. The data are based on calculation of the average increase in skin darkening based on skin color changes measured by the colorimeter "L" or light-dark value [($\Delta$ L)]; the average increase in skin hue intensity measured simultaneously by both the colorimeter "a*" or red value and the colorimeter "b*" or yellow value ($\Delta\sqrt{a^2+b^2}$); and, the average increase in total tan which adds the changes in darkness and hue increases [($\Delta$ L)+$\Delta\sqrt{a^2+b^2}$].

TABLE 13

| Formula | Darkness increase ($\Delta$L) | Hue increase $\Delta\sqrt{a^2 + b^2}$ | Tan Increase ($\Delta$L) + $\Delta\sqrt{a^2 + b^2}$ |
| --- | --- | --- | --- |
| A | 4.4 | 7.4 | 11.8 |
| B | 3.4 | 8.0 | 11.4 |
| C | 2.1 | 4.4 | 6.5 |
| D | 2.8 | 4.4 | 7.2 |
| E | 4.0 | 3.0 | 7.0 |
| G | 4.0 | 3.7 | 7.7 |
| H | 3.9 | 4.1 | 8.0 |
| J | 4.1 | 2.9 | 7.9 |
| Baseline A-D | n/a | n/a | n/a |
| Baseline E-J | n/a | n/a | n/a |

Formulas A and B of Tables 11, 12 and 13 contained either pentylene glycol or isopentyl diol added to DHA and MSM and were calculated as significantly darker than the control formula (E) containing only DHA and MSM. The objective results were confirmed with visual grading. None of the other additives evaluated in this series were shown to be significantly darker or lighter than the control.

Throughout the above studies as well as during consumer evaluation of sunless tanning formulas containing DHA and MSM, panelists have remarked on the lack of odor associated with these formulations, both during initial application and during the period following application. As an example of the lack of odor associated with the MSM/DHA formulations, two formulations containing a relatively high level of DHA (10%), with and without MSM were evaluated by 40 volunteers over the course of a week. Each formula was applied as a fine spray to cover legs, torso, arms and face and allowed to dry. Panelists were instructed not to shower or bathe for at least six hours following application. Panelists rated the initial bronzing color and the color of the sunless tan development for tan intensity, evenness, and natural-looking color over the course of one week. In this evaluation, Product formula 24-119B, shown in Exhibit I, was applied and evaluated for one week.

Approximately two weeks after the first test, the same panelists applied the second product and evaluated this product formula 24-191, shown in Exhibit II.

Panelists rated formula 24-191 as developing a darker tan and lasting longer versus formula 24-119B and the majority of panelists commented on the lack of odor for formula 24-191 versus an unpleasant odor for formula 24-119B. The results from this consumer study showed Formula 24-191 with MSM, DHA and pentylene glycol to be significantly preferred over a control formula 24-119B containing the same level of DHA but containing glycerin and no pentylene glycol or MSM. Both formulas contain 10% DHA.

Exhibit I

Formula #24-119-B

| Ingredient | % W/W |
| --- | --- |
| Water and stabilized Aloe Vera Gel | 69.89 |
| Ethoxydiglycol | 1.00 |
| Dihydroxyacetone | 10.00 |
| Glycerin | 5.00 |
| Sorbitol Solution 70% | 2.00 |
| Polysorbate 20 | 0.50 |
| Citric Acid Sol'n 25% | 1.26 |
| FD&C Yellow # 5 (50:50 water/butylenes glycol) 1% | 1.75 |
| FD&C Red # 40 (50:50 water/butylenes glycol) 1% | 2.04 |
| FD&C Red # 33 (50:50 water/butylenes glycol) 2.5% | 0.51 |
| FD&C Green # 5 (50:50 water/butylenes glycol) 1% | 3.50 |
| Sodium Citrate Solution 25% | 1.35 |
| DMDM Hydantoin | 0.20 |
| Alcohol SDA 40, 200 Proof | 1.00 |

Exhibit II

Formula #24-191

| Ingredient | % W/W |
| --- | --- |
| Simethicone | 0.01 |
| Methylsulfonyl Methane | 5.00 |
| Dihydroxyacetone | 10.00 |
| Pentylene Glycol | 5.00 |
| Butylene Glycol | 1.20 |
| Polysorbate 20 | 0.60 |
| Citric Acid Solution, 25% w/w | 1.21 |
| FD&C Yellow # 5 (50:50 water/butylene glycol) 1% | 1.76 |
| FD&C Red # 40 (50:50 water/butylene glycol) 1% | 2.32 |
| FD&C Red # 33 (50:50 water/butylene glycol) 2.5% | 0.41 |
| FD&C Green # 5 (50:50 water/butylene glycol) 1% | 3.50 |
| Sodium Citrate Solution, 25% w/w | 0.56 |
| Phenoxyethanol | 0.30 |
| Aloe Vera Gel | 0.10 |
| Water, Deionized,; add sufficient amount to make | 100.00 |

While the examples set forth above illustrate specific embodiments of the invention and should be considered non-limiting examples with variations and modifications thereof, all being within the spirit and purview of this invention.

What is claimed is:

1. An improved self-tanning formulation consisting of
   (a) methyl sulfonylmethane at a concentration of 1%-20% by weight, based on the total weight of the formulation,
   (b) 1,3-dihydroxyacetone, at a concentration of 0.5%-20% by weight, based on the total weight of the formulation
   (c) at least one shelf-stable solvent selected from the group consisting of water, ethanol, and volatile organic silicones,
   wherein the formulation is in a form selected from the group consisting of a liquid, a foam, a lotion, and a cream, and wherein the improvement consists of
   (d) the inclusion in the formulation, as the sole self-tan enhancing glycol humectant either (i) 1,2-pentanediol alone or (ii) 1,2-pentanediol in combination with one or both of isopentyldiol or hexylene glycol.

2. The improved self-tanning formulation of claim 1 wherein methyl sulfonylmethane is present at a concentration of about 5% by weight, based on the total weight of the formulation.

3. The improved self-tanning formulation of claim 1 wherein methyl sulfonylmethane and 1,3-dihydroxyacetone are present at a ratio of about 1:1.

4. The improved self-tanning formulation of claim 1 wherein the sole self-tan enhancing glycol humectant is present at a concentration of from about 4% to about 8% by weight, based on the total weight of the formulation.

5. An improved self-tanning formulation consisting of
   (a) methyl sulfonylmethane at a concentration of 1%-20% by weight, based on the total weight of the formulation,
   (b) 1,3-dihydroxyacetone, at a concentration of 0.5%-20% by weight, based on the total weight of the formulation
   (c) at least one shelf-stable solvent selected from the group consisting of water, ethanol, and volatile organic silicones,
   wherein the formulation is in a form selected from the group consisting of a liquid, a foam, a lotion, and a cream, and wherein the improvement consists of
   (d) the inclusion in the formulation of isopentyldiol as the sole self-tan enhancing glycol humectant
   and further wherein the improved self-tanning formulation produces a tan that is darker, more even and longer-lasting.

6. The improved self-tanning formulation of claim 5 wherein methyl sulfonylmethane is present at a concentration of about 5% by weight, based on the total weight of the formulation.

7. The improved self-tanning formulation of claim 5 wherein methyl sulfonylmethane and 1,3-dihydroxyacetone are present at a ratio of about 1:1.

8. The improved self-tanning formulation of claim 5 wherein the sole self-tan enhancing glycol humectant is present at a concentration of about 8%.

* * * * *